United States Patent [19]

Matsuda et al.

[11] Patent Number: 5,090,423
[45] Date of Patent: Feb. 25, 1992

[54] LOCAL HEATING APPARATUS AND CAVITY RESONATOR FOR LOCAL HEATING

[75] Inventors: Jinichi Matsuda; Kazuo Kato, both of Niigata, Japan

[73] Assignees: Omron Corporation; Jinichi Matsuda; Kazuo Kato; Yoshiaki Saito, all of Kyoto, Japan

[21] Appl. No.: 425,203
[22] PCT Filed: Feb. 17, 1989
[86] PCT No.: PCT/JP89/00163
§ 371 Date: Oct. 6, 1989
§ 102(e) Date: Oct. 6, 1989
[87] PCT Pub. No.: WO89/07469
PCT Pub. Date: Aug. 24, 1989

[30] Foreign Application Priority Data

Feb. 18, 1988 [JP] Japan .................. 63-34049

[51] Int. Cl.$^5$ .............................................. A61N 5/02
[52] U.S. Cl. ...................... 128/804; 128/783; 128/400; 600/9; 600/10; 600/14
[58] Field of Search ............ 128/804, 783, 373, 400; 600/9, 10, 13, 14; 606/27, 28; 219/10.55 R, 10.55 F, 10.55 A; 333/227

[56] References Cited

U.S. PATENT DOCUMENTS

| | | | |
|---|---|---|---|
| 3,090,018 | 5/1963 | Foss | 333/227 |
| 3,336,142 | 8/1967 | Lawson | 219/10.55 A |
| 3,384,814 | 5/1968 | Stinehelfer | 333/227 |
| 3,422,240 | 1/1969 | Parker | 219/10.55 F |
| 3,521,019 | 2/1968 | White | 219/10.55 F |
| 3,555,232 | 1/1971 | Bleackly | 219/10.55 A |
| 3,597,566 | 8/1971 | Johnson et al. | 219/10.55 A |
| 4,053,856 | 10/1977 | Fisher et al. | 333/227 |
| 4,434,341 | 2/1984 | Busby | 128/804 |
| 4,589,424 | 5/1986 | Vaquine | 219/10.55 F |
| 4,589,516 | 5/1986 | Turner | 128/804 |
| 4,672,980 | 6/1987 | Turner | 128/804 |
| 4,674,481 | 6/1987 | Boddie, Jr. et al. | 600/10 |
| 4,726,071 | 2/1988 | Jachowski | 333/17.1 |
| 4,745,246 | 5/1988 | Hori et al. | 219/10.55 F |
| 4,798,215 | 1/1989 | Turner | 128/804 |
| 4,816,632 | 3/1989 | Claesson et al. | 219/10.55 F |
| 4,867,175 | 9/1989 | Takase | 128/804 |

FOREIGN PATENT DOCUMENTS

| | | |
|---|---|---|
| 60-4516 | 1/1985 | Japan . |
| 209672 | 9/1986 | Japan . |
| 62-2060 | 1/1987 | Japan . |

Primary Examiner—Edward M. Coven
Assistant Examiner—Jessica J. Harrison
Attorney, Agent, or Firm—Griffin Branigan & Butler

[57] ABSTRACT

A heating apparatus suitable for use in medical heat treatment of an affected portion of a human body employs a cavity resonator supplied with high-frequency energy from a high-frequency power supply unit. The cavity resonator comprises a cavity formed of a conductive material and at least one inner protrusion in said cavity generating a standing wave electric field for heating a body or body part introduced into the cavity. The inner protrusion may be a separate conductor or may be formed by deforming a portion of the conductor forming the cavity. A highly concentrated standing wave electric field and a surrounding electromagnetic field are produced in the cavity resonator when it is energized from the high-frequency power supply unit. The concentrated standing wave electric field intensively heats a desired local portion of the body and deep parts of the body may be heated satisfactorily.

13 Claims, 9 Drawing Sheets

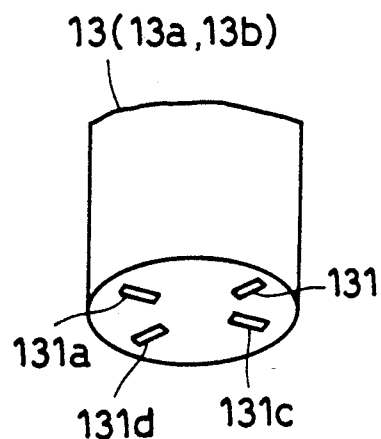
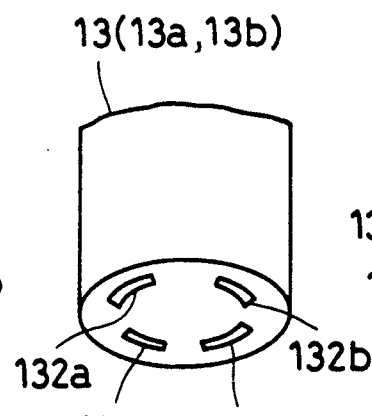
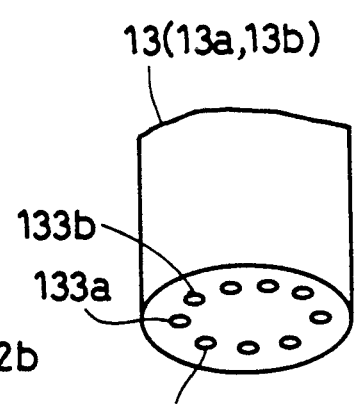
FIG. 5a   FIG. 5b   FIG. 5c
Fig. 6
Fig. 7
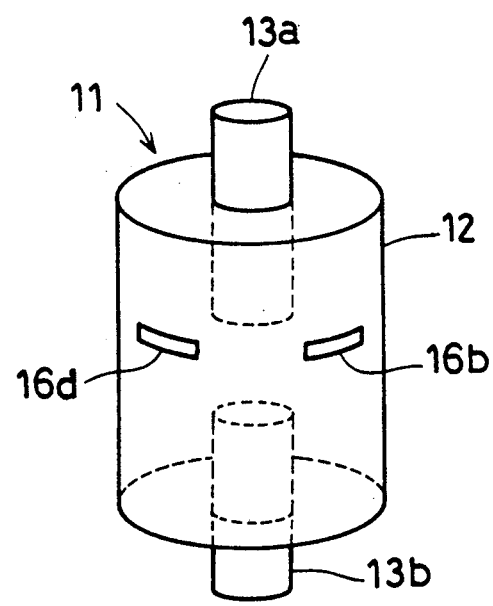
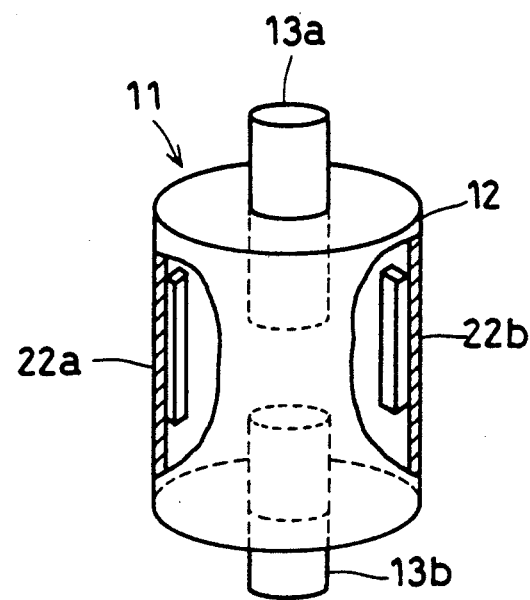

LOCAL HEATING APPARATUS AND CAVITY RESONATOR FOR LOCAL HEATING

FIELD OF THE INVENTION

The present invention relates to a heating apparatus which can heat a body satisfactorily up to a deep portion thereof and heat a desired portion intensively, and specifically relates to a local heating apparatus which supplies high-frequency energy to a cavity resonator, and heats a local portion by a standing wave electromagnetic field generated by that energy.

BACKGROUND OF THE INVENTION

Local heating which heats a specific portion has been performed extensively in various technical fields. For example, in the field of medical treatment, treatments of blood circulation disorders, inflammation disease, neuralgia and the like are performed by applying high-frequency energy to an affected portion of a human body. Also, recently, it is known that cancer cells perish by heating cancer tissue to 43° C. or more, and therefore medical treatment of cancer which locally heats the cancer tissue portion has been performed.

FIG. 20 shows a basic configuration of a conventional local heating apparatus which heats a human body for the purpose of treatment of cancer.

A pair of plane electrodes 91 and 92 are installed in a manner of sandwiching an affected portion 81. When high-frequency energy is applied to a pair of the plane electrodes 91 and 92 from a high-frequency power supply unit 93, the affected portion 81 is heated between the plane electrodes 91 and 92.

In this case, a fat layer exists on the surface of the human body, and this fat layer is particularly easy to be heated since it is positioned beneath the electrodes, and therefore cooling parts 94 and 95 are installed beneath the plane electrodes 91 and 92, and cooling water is circulated by a cooling apparatus 96. Thereby, the human body is prevented from suffering any adverse effect by unnecessary heating of the fat layer.

Conventional local heating apparatus using a pair of plane electrodes tends to heat the tissue having a high electric resistance, like the fat layer on the surface of the human body, more intensely than the tissue having a low electric resistance, and a deeper part of the human body apart from the electrode is harder to heat because the electric field (or displacement current) diffuses as it enters the human body. For this reason, there exist problems such that heating concentrated on a local portion is difficult to perform. Furthermore, local scalding of the normal tissue in the surface fat portion may result from long periods of heating.

For example, when the cancer tissue is heated at 43° C. or higher, cells of cancer perish, but when the cells of cancer existing in the deep part of the human body are intended to be heated to 43° C. or higher, in the conventional local heating apparatus, there is a risk that the tissue close to the plane electrode is heated to 45° C. or higher which is the limit temperature thereof, and therefore, the cells of cancer located in the deep part cannot be heated satisfactorily. Thus, in conventional local heating apparatus, it is the present state that only the cancer existing near the surface of the human body can be treated.

Accordingly, the present invention provides a local heating apparatus which eliminates the deficiency of conventional local heating apparatus. The present invention provides apparatus for heating deep-seated parts of a body and for intensively heating a desired local portion, and a cavity resonator for local heating suitable for use in the apparatus.

SUMMARY OF THE INVENTION

An object of the invention is to realize concentrated heating of a deep portion of a human body by generating a highly concentrated and stable standing wave electric field by the function of wall current in the cavity resonator and an incidental high frequency electromagnetic field.

To generate an electric field the cavity resonator for local heating of the present invention has a basic configuration such that a cavity is formed from a conductor, and an inner protrusion applying a standing wave electric field onto a body to be heated is formed by deforming part of the conductor forming the cavity into the cavity or by a separate conductor. When high frequency energy is applied to the cavity resonator having this configuration and a resonance is generated in the cavity, a concentrated standing wave electric field is generated between the inner protrusion and the conductor of the cavity opposing thereto, or between two inner protrusions where they are displaced in an opposite fashion, and a strong magnetic field and current on the inner cavity wall are generated so as to surround the electric field.

The strong magnetic field and the wall current confine the electric field to prevent diffusion thereof, and generate a strong standing wave electric field concentrating on the center axis between the inner protrusion and the conductor opposing thereto or between the inner protrusions.

Thus, the heating can be performed satisfactorily up to the deep part of the body to be heated.

Also, the local heating apparatus of the present invention adopts a basic configuration that the above-mentioned cavity resonator is provided with a high-frequency power supply unit.

By this configuration, heating can be performed satisfactorily up the deep part of the body to be heated, and a desired local portion can be heated intensively without scalding the normal tissue of the surface.

BRIEF DESCRIPTION OF THE DRAWINGS

FIGS. 5a, 5b and 5c illustrate first, second and third arrangements, respectively, of holes in an inner protrusion to vary distribution of an electric field;

FIG. 6 illustrates a cavity resonator having holes in the cavity wall for varying the distribution of an electric field;

FIG. 7 shows a cavity resonator having members disposed in the cavity for adjusting the distribution of an electric field;

DETAILED DESCRIPTION OF THE INVENTION

Figure 1A:
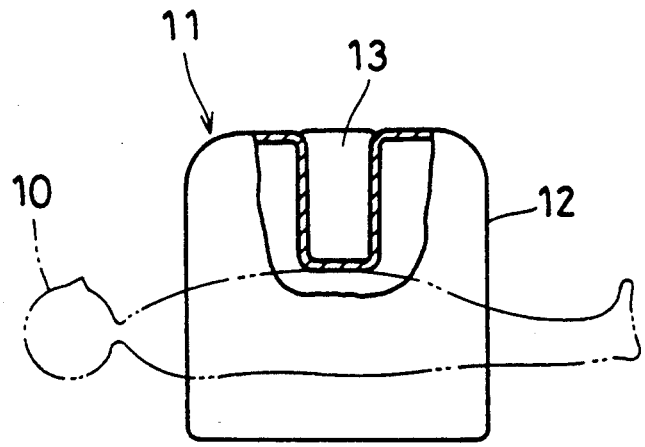
FIG. 1a illustrates a basic configuration a cavity resonator suitable for use in practicing the present invention, the cavity resonator having an inner protrusion formed from a portion of the cavity wall.

For the sake of convenience in description, various embodiments of a cavity resonator for local heating will be described after which various embodiments of a local heating apparatus will be described. Like reference numerals are used to identify like elements throughout the drawings.

As shown in FIG. 1a, a first embodiment of a cavity comprises an inner protrusion 13 formed by deforming part of a cavity 12 which is made of a conductor material. Alternatively, inner protrusion 13 may be a separate conductor cylinder or a conductor rod as shown in FIG. 1b.

A body 10 to be heated is carried in between the inner protrusion 13 and the lower wall of the cavity 12. The cross-section of the inner protrusion 13 can be circular, elliptic or rectangular in shape.

It is well known that a cavity resonator electrically starts resonance at a particular frequency generally referred to as the resonant frequency. This resonant frequency is dependent on the dimensions and inner shape of the cavity, the material of which the cavity is made, and so on. When resonance is started, a standing wave electric field, a magnetic field and a wall current are simultaneously excited in the cavity resonator. A relationship represented by Maxwell's equation exists between the electric field, the magnetic field and the wall current with the two fields being inter-related through the wall current. Accordingly, when the intensity or distribution of the electric field in the cavity resonator begins to change, the wall current immediately works to suppress the change, and the intensity or distribution of the magnetic field around the electric field is changed. This mechanism permits the standing wave electric field in the cavity to be stably confined. Thus, when high-frequency energy is supplied to the cavity resonator 11 from an external source so that the cavity 12 resonates, a strong standing wave electric field E (FIG. 1c) is generated between the inner protrusion 13 and the wall of cavity 12 facing the protrusion 13 as shown in FIG. 1c. A strong magnetic field H and current on the inner cavity wall are generated so as to surround the electric field E. This strong magnetic field H and the current on the inner cavity wall confine the standing wave electric field E so that it does not diffuse, and gives a strong standing wave electric field concentrating on the center axis of the inner protrusion 13.

Figure 1B:
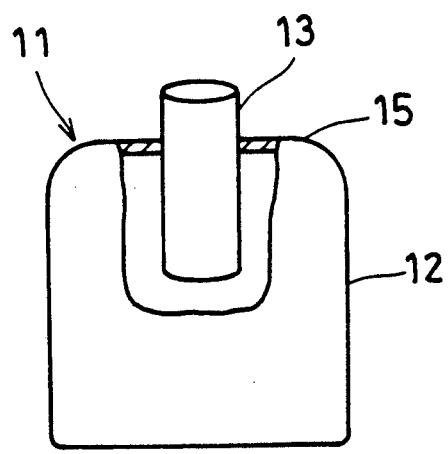
FIG. 1b shows a cavity resonator with a separately formed inner protrusion.
Figure 1C:
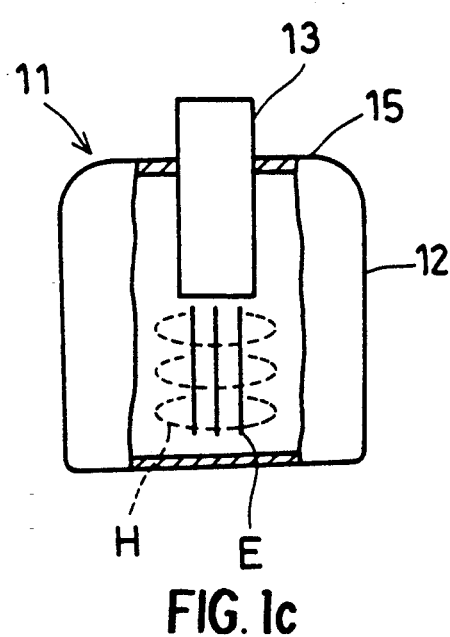
FIG. 1c illustrates the electromagnetic and standing wave electric fields produced in the cavity resonators of FIGS. 1a and 1b.
Figure 2A:
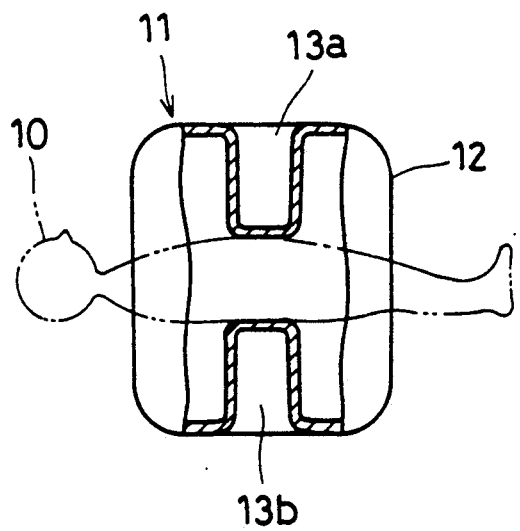
FIG. 2a illustrates a modification of the cavity resonator of FIG. 1a, the cavity resonator being provided with opposing inner protrusions formed from portions of the cavity wall.
Figure 2B:
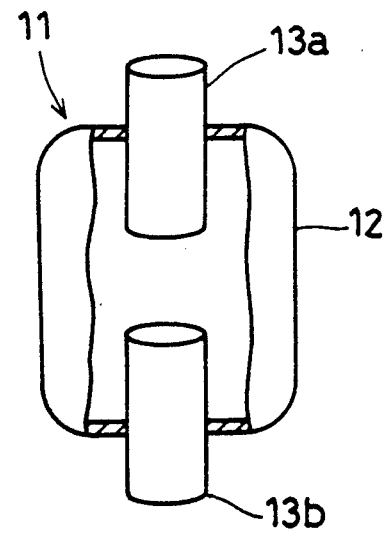
FIG. 2b illustrates a modification of the cavity resonator of FIG. 1b, the cavity resonator being provided with opposing inner protrusions which are conductors separate from the cavity wall.

In the embodiment of FIGS. 1a and 1b, the bottom wall of the cavity 12 serves as a second protrusion. However, a second embodiment the resonant cavity may be provided with two inner protrusions 13a and 13b arranged to face each other. As shown in FIG. 2a the inner protrusions 13a and 13b may be formed by deforming part of the conductor of the cavity 12, or as shown in FIG. 2b the inner protrusions 13a and 13b may comprise separate conductors such as conductor cylinders or conductor rods. In addition, it is also possible that one of the inner protrusions 13a and 13b may comprise a hollow and the other may comprise a conductor cylinder or conductor bar.

The body 10 to be heated is carried between the inner protrusions 13a and 13b. This configuration can raise the degree of concentration of the electric field for heating and improve the heating effect.

Also, when the human body is heated using the cavity resonator 11, as described later in the item of heating experiment, a new effect is obtained that heating of the tissue having a high electric resistance, such as the fat layer and bones not wanted to be heated, is suppressed to a low degree, and the cancer tissue which is the target of treatment is heated effectively so that the effect of treatment is greatly improved. Also, since the space to be heated can be made cylindrical between the inner protrusions 13a and 13b and the diameter of the portion to be heated is reduced to a small value, the risk of heating the normal tissue is decreased to a great extent in comparison with the conventional technology. Thus, this configuration has an effect capable of solving the problem peculiar to heating the human body.

Figure 3:
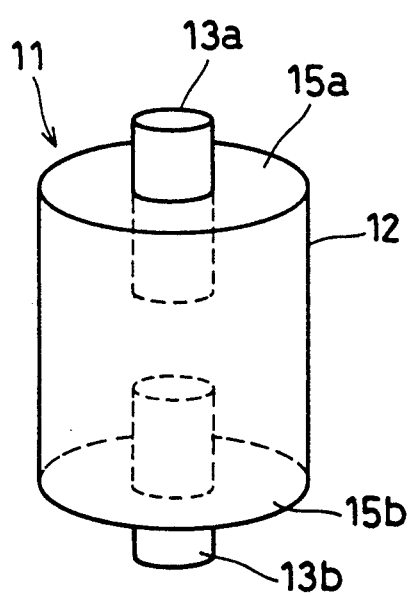
FIG. 3 illustrates a cylindrical cavity resonator with cylindrical inner protrusions supported by end surfaces of the cavity.

The cavity 12 may comprise a cylindrical conductor as shown in FIG. 3, with inner protrusions 13 (13a and 13b) installed on its end surface 15 (15a and 15b). For the cavity resonator constituted with the cavity 12 of this cylindrical conductor, for example, there is the reentrant-type resonator. FIG. 3 shows an embodiment wherein the inner protrusions 13a and 13b comprise two conductors facing each other. By installing the inner protrusions 13 on the end surfaces as shown, a nice state of resonance is obtained, a highly concentrated standing wave electric field is generated between the inner protrusions, and the heating effect can be improved.

Figure 4:
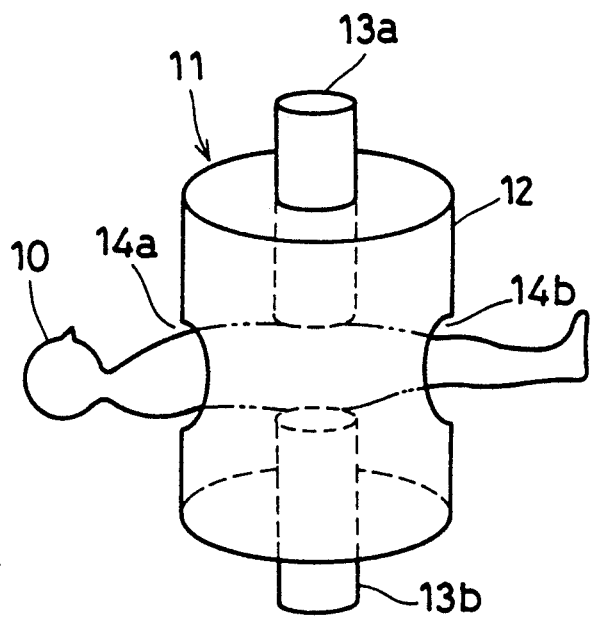
FIG. 4 illustrates a cavity resonator having openings through which a body or body part may be inserted into, or removed from, the cavity.

As shown in FIG. 4, cavity 12 may be provided with entrances 14 (14a and 14b) for admitting or removing the body 10 to be heated. Where the whole of the body 10 is put in the cavity 10, one entrance 14 will do. In this case, when an open-close lid (not shown) of a conductor material is attached to the entrance, the high-frequency current flows also along the inner wall of the open-close lid in the same manner as before providing the entrance is closed. The electromagnetic field in the cavity 12 is not disturbed, and a nice state of resonance can be realized. In addition, the electromagnetic field is prevented from leaking outside the cavity at heating, and safety is insured.

When the protrusion surface of the inner protrusion 13 is formed so as to produce a variable distribution of the electric field, the concentration of the electric field is alleviated and the heating region can be widened.

Variable distribution of the electric field can be realized, for example, by installing surface discontinuities such as slits or recesses or protuberances 131a-131d on the protrusion surface in the radial direction as shown in FIG. 5a, by installing slits or recesses or protuberances 132a-132d on the protrusion surface in the circumferential direction as shown in FIG. 5b, or by installing small holes 133a-133n on the protrusion surface in the circumferential direction as shown in FIG. 5c.

The shape, position, number and the like of these slits, recesses, protuberances or holes are selected properly in correspondence to the range of the heating region.

Also, variable distribution of the electric field can be realized by making the diameter of the inner protrusion 13 larger, particularly the diameter of the tip or end portion. Alternatively, the shape of the inner protrusion 13, particularly the shape of the tip portion thereof, may be elliptically or otherwise formed to match the range of the heating region. Finally, the tip portion of the inner protrusion 13 may be formed by dividing it into a plurality of pieces.

The tip portion of the inner protrusion may comprise a removable adaptor having any of the above-described configurations for producing variable distribution of the electric field. A tip adaptor suitable for the range of the heating region may then be selected and attached to the inner protrusion. Also, where two or more inner protrusions (13a and 13b) are installed, it is also effective if at least one of them is structured to provide variable distribution of the electric field.

Thus, the provision of an inner protrusion structure producing a variable electric field makes it possible to adjust the range of concentration of the electric field, and one can expand the heating region corresponding to the range of the portion to be heated. For example, when the diameter of the cancer tissue is as small as several cm or less, heating can be performed nicely by a combination of the cavity resonator 11 and the inner protrusions 13. However, for a larger cancer tissue, the whole of the large cancer tissue can be heated nicely by expanding the range of concentration of the electric field by means of a protrusion which produces a variable distribution of the electric field.

Adjustment of the range of concentration of the electric field formed by the inner protrusions 13 (13a and 13b) shown in FIG. 6, can be realized by providing electric field distribution adjusting holes 16 (16a and 16b) in part of the conductor constituting the cavity 12. By providing the electric field distribution adjusting holes 16 (16a and 16b), the whole distribution of electromagnetic field in the cavity 12 is changed, and attending on this change, the range of concentration of the electric field formed by the inner protrusions 13 (13a and 13b) is changed.

As shown in FIG. 7, adjustment of the range of concentration of the electric field formed by the inner protrusions 13 (13a and 13b) is realized by providing electric field adjusting members 22 (22a and 22b) in the cavity 12.

The electric field adjusting members 22 (22a and 22b) may comprise conductors, dielectrics or the like, and work effectively when installed at places of a high electric field intensity in the cavity 12. These electric field adjusting members 22 (22a and 22b) change the whole distribution of the electromagnetic field in the cavity 12, and thus change the range of concentration of the electric field formed by the inner protrusions 13 (13a and 13b).

The shape, number and positions of mounting of the electric field adjusting members 22 (22a and 22b) are selected properly in correspondence to the range of the heating region.

The resonance frequency of the cavity resonator 11 varies depending on the volume and shape of the cavity. Accordingly, as shown in FIG. 8, resonance frequency can be changed by making part of the conductor constituting the cavity 12 movable.

Figure 8:
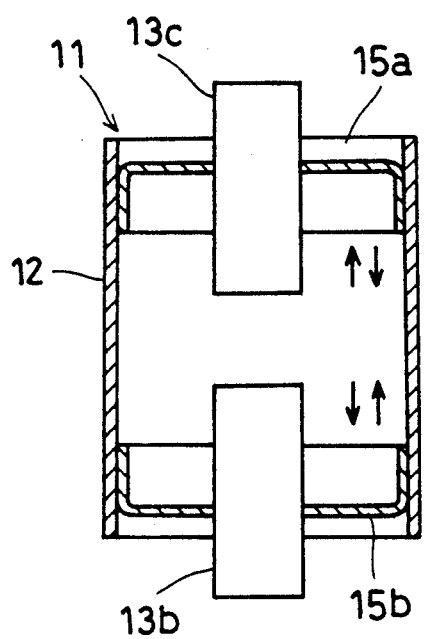
FIG. 8 shows a cavity resonator with movable end surfaces for varying the resonance frequency.

In FIG. 8, the top and bottom end surfaces 15a and 15b of the cylindrical cavity 12 are both made movable but only one of the end surfaces 15a and 15b need be made movable. Where the cavity 12 is rectangular, the side surface may be made movable. This configuration makes it possible to arbitrarily adjust the resonance frequency of the cavity resonator 11 and as a result the best frequency can be selected corresponding to the heating condition desired.

The thickness of the body 10 to be heated varies depending on each body to be heated, and it is preferable to maintain the space between the surface of the inner protrusion 13 and the body 10 to be heated in the best state all the time. This may be accomplished by making at least one of the inner protrusions 13a and 13b in the form of an adjustable conductor cylinder or conductor rod.

Figure 9:
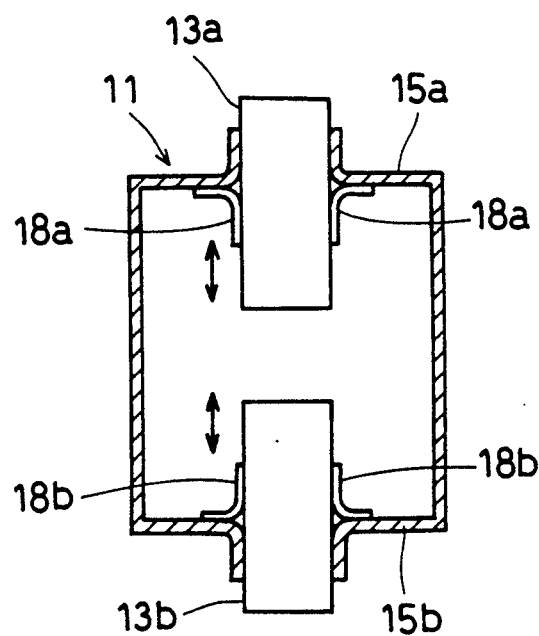
FIG. 9 shows a cavity resonator with movable inner protrusions.

FIG. 9 shows an example of a structure permitting variable positioning of the protrusion surfaces. The inner protrusions 13a and 13b comprise conductors which are slidably mounted in the end surfaces 15a and 15b of the cavity so as to be capable of moving up and down.

Up-down movement of the inner protrusions 13a and 13b can be accomplished in various ways. The density of the high-frequency current flowing through the portion of contact of the inner protrusions 13a and 13b with the end surfaces 15a and 15b of the cavity is large and there is a large power loss unless a good contact is maintained between the protrusions and the end surfaces. To prevent this power loss, contact members 18a and 18b comprising slidable and highly conductive spring material are attached to the end surfaces 15a and 15b, and the inner protrusions 13a and 13b move up and down while sliding on contact members 18a and 18b. Although FIG. 9 shows two slidable protrusions, only one of the inner protrusions 13a and 13b may be made movable up and down.

Figure 10:
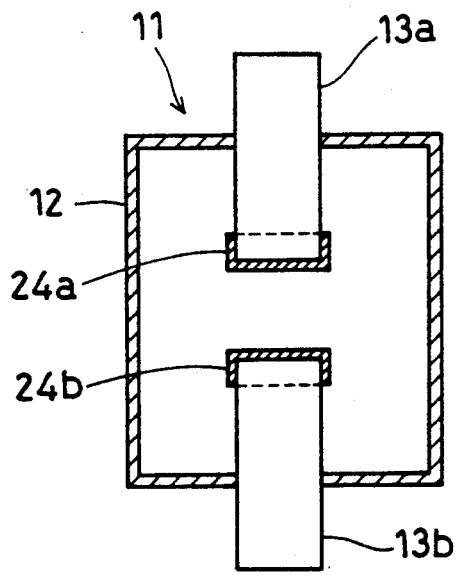
FIG. 10 shows a cavity resonator having electrical insulators on the inner protrusions.

When the output power of the cavity resonator 11 is large, a discharge might occur from the surface of the inner protrusions 13a and 13b. As shown in FIG. 10, this discharge can be prevented by covering the surfaces of the inner protrusions 13 (13a and 13b) with insulating parts 24 (24a and 24b). Insulation is effective even when an insulating part is installed on only one of the inner protrusions 13a and 13b.

Also, a discharge can be prevented by providing a space between the body 10 to be heated and the inner protrusions.

The resonance frequency realizing the best state of resonance of the cavity resonator 11 is critical, and therefore to realize the best state of resonance, fine adjustment of the resonance frequency is required to be made. In addition, if the oscillation deviates from the state of resonance, the output voltage drops, and accordingly the heating ability is also reduced.

Figure 11:
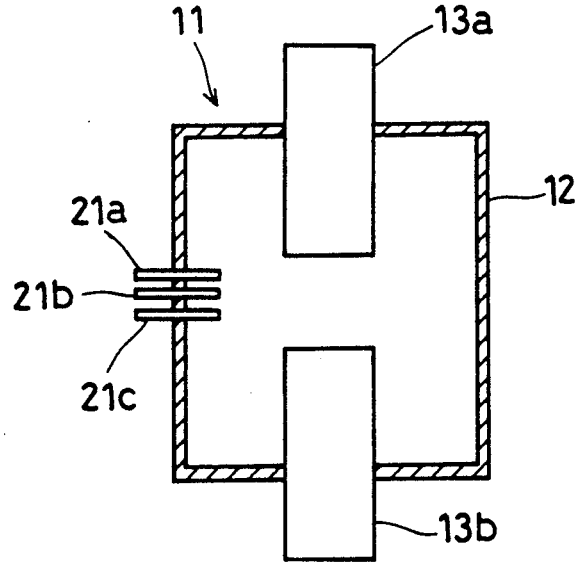
FIG. 11 shows a cavity resonator having adjusting members for fine adjustment of the resonance frequency.

As shown in FIG. 11, to make this fine adjustment of the resonance frequency, frequency adjusting members 21 (21a, 21b and 21c) are mounted in the cavity 12 in a manner capable of insertion.

The frequency adjusting members 21a-21c each comprise a conductor rod, and the effect thereof is large when they are mounted on the portion of cavity 12 near where the intensity of the electric field is high. The number of frequency adjusting members 21 (21a-21c) is selected according to the variable range of frequency required. Also, adjustment of the degree of insertion is made by various methods, and can be made by automatic control as subsequently described.

Figure 12:
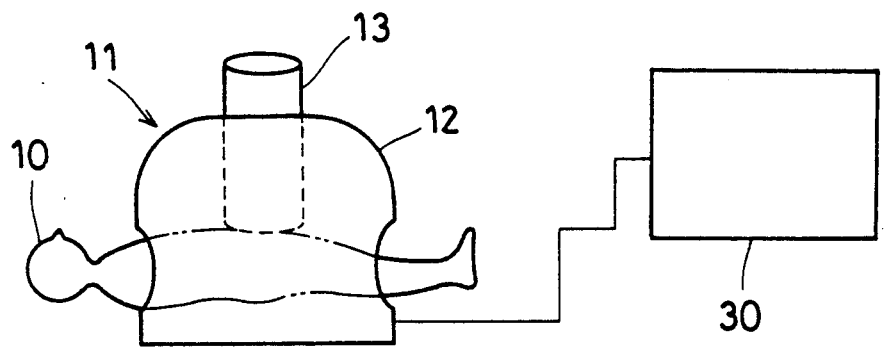
FIG. 12 illustrates a local heating apparatus for heating of a human body.
Figure 13A:
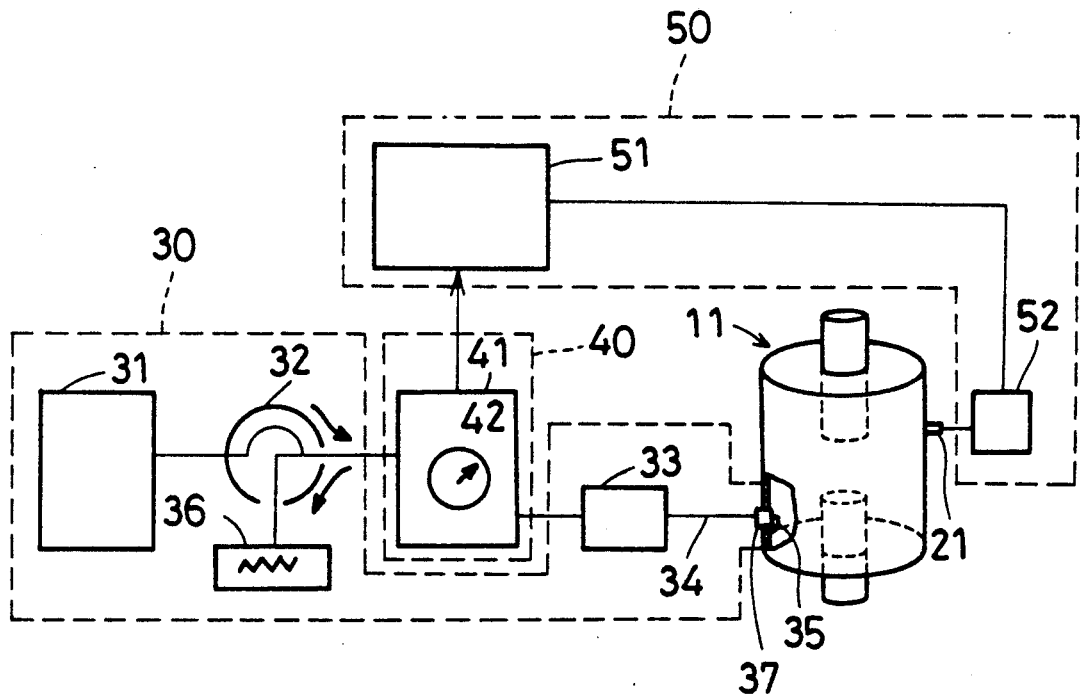
FIG. 13a illustrates a local heating apparatus and its control circuitry.

A local heating apparatus of the present invention may employ any of the cavity resonators 11 described above for local heating. In FIG. 12, the cavity resonator 11 is any one of the cavity resonators for local heating as described above. High-frequency energy is supplied from a high-frequency power supply unit 30 to cavity resonator 11 to put it in the state of resonance. In the resonant state of the cavity resonator 11, a strong standing wave electric field of high concentration is generated between the inner protrusions 13, and the body 10 is thereby heated locally up to a sufficient depth. Also, a desired local portion can be heated intensively without scalding the normal tissue of the surface. The high-frequency power supply unit 30 may be constructed as subsequently described. The local heating apparatus of FIG. 13a employs a cavity resonator 11 having frequency adjusting members 21 as described with reference to FIG. 11. In FIG. 13a, the basic configuration and the operation of the cavity resonator 11, the high-frequency power supply unit 30, and the position controlling means 50 are as described previously.

In the high-frequency power supply unit 30, high-frequency energy generated by a high-frequency energy generator 31 passes through a directional coupler 32, an impedance matching unit 33 and a cable 34, and is supplied to the cavity resonator 11 by coupling it through a coupling probe 35 in the cavity 12.

The impedance matching unit 33 performs impedance matching between the directional coupler 32 and the cavity resonator 11. This matching can also be performed automatically.

The directional coupler 32 delivers the high-frequency energy from the high-frequency energy generator to the cavity resonator 11 side, and delivers the high-frequency energy reflected from the cavity resonator 11 to a resistor 36 thereby preventing the reflected high-frequency energy from entering the high-frequency energy generator and breaking it. A connector 37 is attached to the cavity 12, and connects the cable 34 and the coupling probe 35.

As shown in FIG. 13a the resonant state detecting means 40 may comprise a standing wave detector 41. The standing wave detector 41 is coupled between the directional coupler 32 and the impedance matching unit 33, and detects the standing wave and indicates it by a standing wave indicator 42.

Figure 13B:
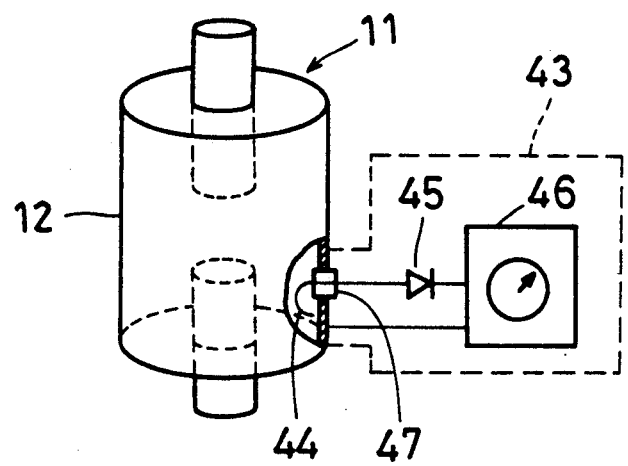
FIG. 13b illustrates an alternative embodiment of the control circuitry.
Figure 16:
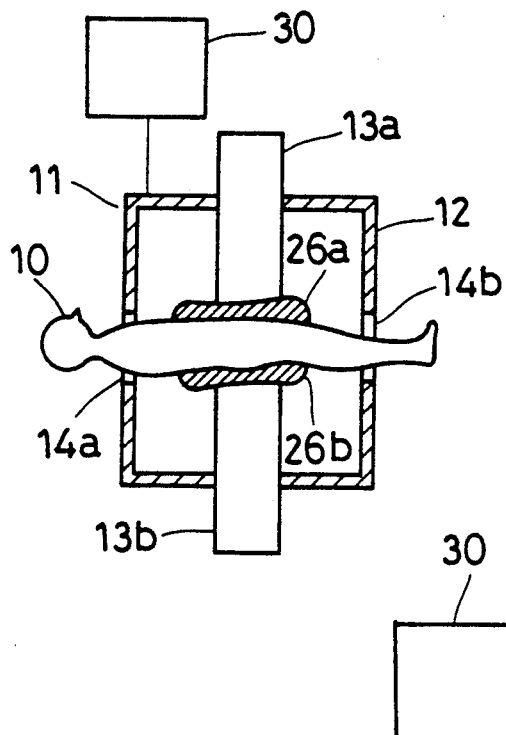
FIG. 16 illustrates a local heating apparatus with gap members for filling the gaps between a body and the inner protrusions.

As shown in FIG. 13b, the resonant state detecting means 40 may comprise an amplitude detector 43. The amplitude detector 43 takes out high-frequency output of the cavity resonator 11 by a detecting probe 44 installed in the cavity 12, converts it into DC by a rectifier 45, and thereafter makes an amplitude indicator 46 indicate the DC value. This DC value indicates the amplitude of high-frequency output of the cavity resonator 11. Numeral 47 designates a connector connecting the detecting probe 44 and the rectifier 45 side.

In the position controlling means 50, numeral 51 designates a detection controlling unit, and numeral 52 designates a driving unit including a motor for making positional adjustments by driving a frequency adjusting member 21.

When the resonant state detected by the resonant state detecting means 40 is applied to the position controlling means 50, the detection controlling unit 51 directs the driving unit 52 to adjust the amount of insertion of the frequency adjusting member 21 into the cavity 12 in correspondence to the detected resonant state. The driving unit 52 turns the motor clockwise or counterclockwise according to a given direction to adjust the amount of insertion of the frequency adjusting member 21 into the cavity 12.

In the standing wave method of adjustment using the standing wave detector 41 of FIG. 13a, the amount of insertion of the frequency adjusting member 21 is controlled to minimize the standing wave ratio or the reflected wave indicated by the standing wave indicator 42. In the amplitude indicating method using the amplitude detector 43 of FIG. 13b, control is performed so that the amplitude value indicated by the amplitude indicator 46 becomes maximum.

Thus, the cavity resonator 11 can be maintained in the best state of resonance at all times and a nice heating can be continued even if a person moves during treatment or the condition of resonance of the cavity resonator 11 is varied by a change in electric constant of the person's body due to a rise in the temperature of the body 10.

Also, the electromagnetic field distribution in the resonator is sometimes disturbed by a change in the electric constant or the like, resulting in a pain or a local scald of the human body or a breakage of the high-frequency energy generator 31, but these troubles can also be prevented, and a safe and effective heating or treatment can be performed.

The output power is maximum in the resonant state, and when the frequency of the high-frequency energy supplied to the cavity resonator 11 deviates from the resonance frequency, the output power for heating is reduced. Accordingly, the output power for heating by the cavity resonator 11 can be adjusted by varying the frequency of the high-frequency energy supplied to the cavity resonator 11.

Varying the frequency of high-frequency energy supplied to the cavity resonator 11 can be easily realized by modifying the high-frequency energy generator 31 of the high-frequency power supply unit 30 to make it a variable frequency generator. Furthermore, where the high-frequency energy generator 31 can vary its output stepwise, it is possible to use frequency adjustment as described above so that the output of high-frequency energy can be adjusted continuously from a low level to a high level over a wide range.

Accordingly, the output power, that is, the heating ability of the cavity resonator 11 can be adjusted over a wide range.

When the electric field leaks from the inner protrusion 13, portion other than the heated portion of the body 10 to be heated are heated, and a harmful action might occur.

Figure 14:
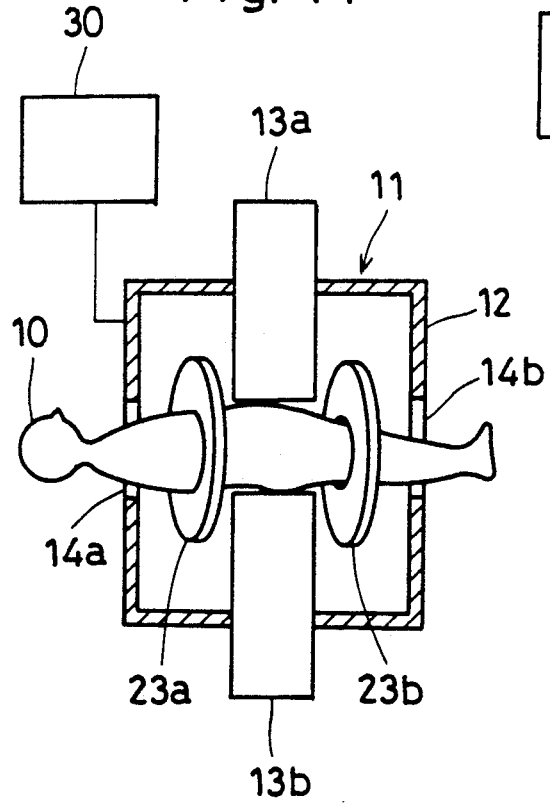
FIG. 14 shows a local heating apparatus with shields for limiting leakage of the electric field.

To prevent this trouble as shown in FIG. 14, shielding members 23 (23a and 23b) are installed in the cavity to cut off leakage of the electromagnetic field to portions other than the heated portion of the body 10 to be heated.

Figure 15:
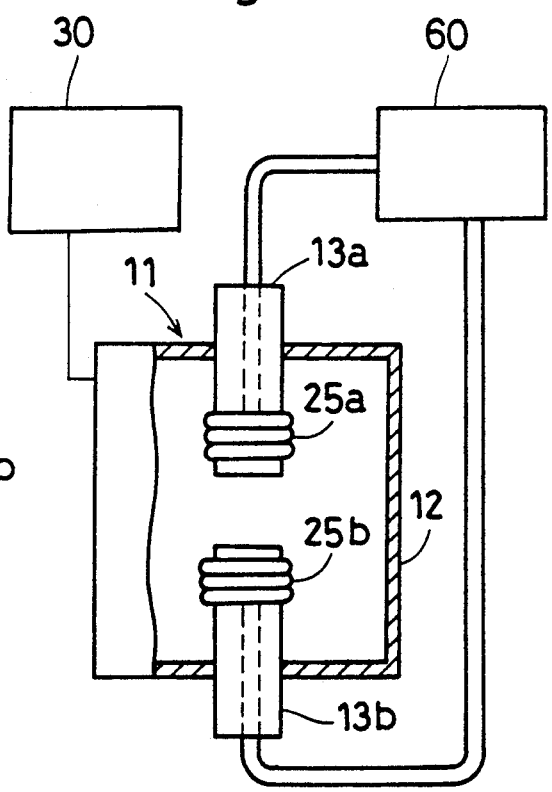
FIG. 15 shows a local heating apparatus with a cooling system for cooling the inner protrusions of the resonant cavity.

The shielding members 23 (23a and 23b) are constituted with a conductor or a dielectric, and either one of the members 23a and 23b will do for this purpose, and further the members can be increased in number.

Where the output power of the cavity resonator 11 is large, the inner protrusion 13 rises in temperature and generates heat, and when the body 10 to be heated is a human body, a scald might occur. To prevent this problem, as shown in FIG. 15, cooling members 25 (25a and 25b) are installed at end portions of the inner protrusions 13 (13a and 13b), and cooling water is circulated by a cooling unit 60. The cooling members 25 (25a and 25b) may comprise, for example, cooling pipes attached to the outside of the inner protrusions (13a and 13b) by winding them around the electrodes or they may be attached to the insides of the inner electrodes. Either one of the cooling members 25 (25a and 25b) will suffice for an effective cooling operation.

Figure 17:
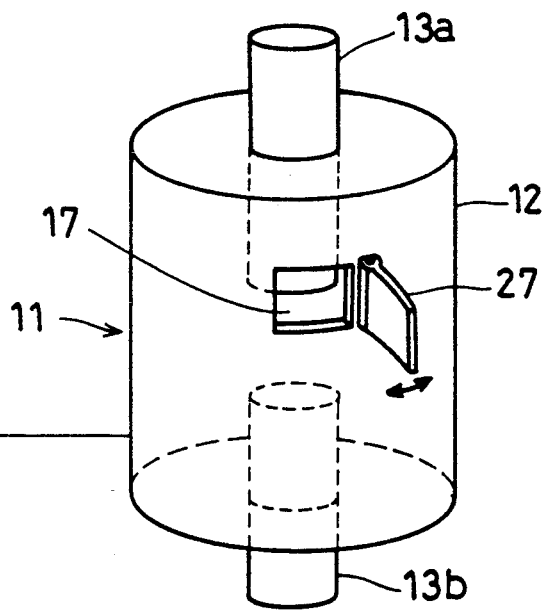
FIG. 17 illustrates a local heating apparatus with an inspection door in the cavity resonator.
Figure 20:
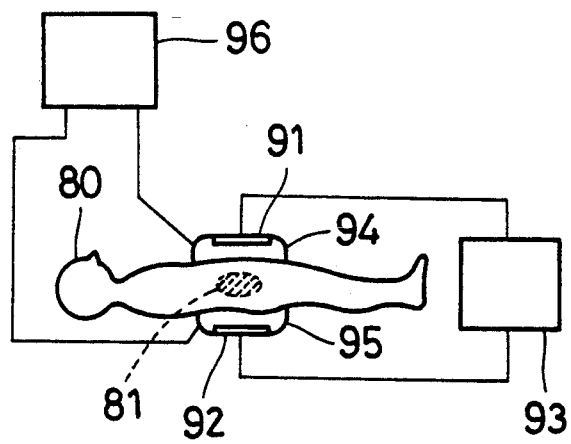

To facilitate attachment and positional adjustment of the gap members 26 (26a and 26b) and check and adjustment of each part in the cavity 12, at least one window having a conductive open-close lid 27 is installed in the cavity 12 as shown in FIG. 17. When the conductive open-close lid 27 is installed, the lid 27 is closed during heating so that a high-frequency current also flows through the lid 27 and turbulence of the electromagnetic field due to the window 17 is suppressed. Also, open-close lid 27 prevents the electromagnetic wave from leaking outside the cavity 12 and thereby a safe treatment can be secured.

When cylindrical heating regions are overlapped by rotating the cavity resonator 11 relative to the body to be heated, the desired local portion can be heated more intensively, and if the cavity resonator 11 is made rotatable relative to the body 10 to be heated, the portion to be heated can be arbitrarily selected.

Figure 18:
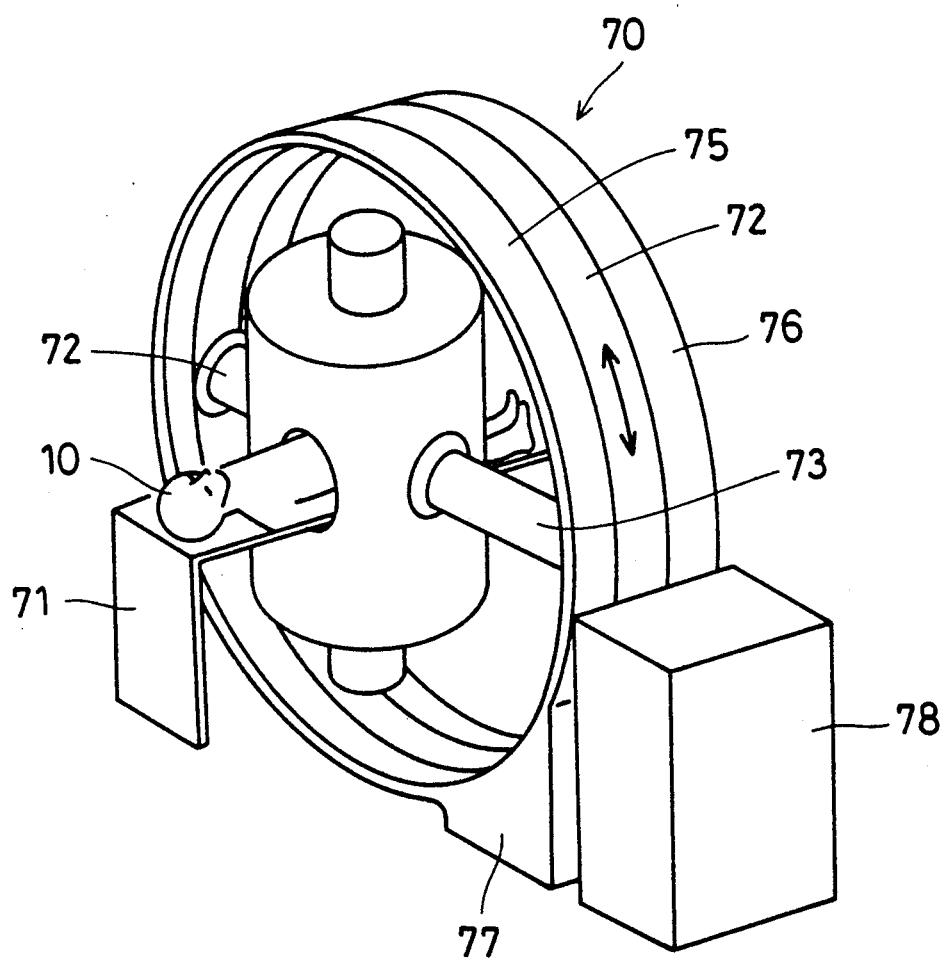
FIG. 18 illustrates a local heating apparatus rotatable about the body to be heated, and a table for inserting or removing the body from the cavity resonator.

In FIG. 18, numeral 71 designates a table for moving a body 10 into and out of the cavity resonator, and numeral 70 designates a rotary mechanism. In the rotary mechanism 70, numeral 72 designates a circular rotary rack, which supports the cavity resonator 11 by support frames 73 and 74. Numerals 75 and 76 designate circular support racks, which rotatably support the rotary rack 72. Numeral 77 designates a fixing leg, which fixes and supports the support racks 75 and 76. Numeral 78 indicates a rotation driving unit, which rotates the rotary rack 72. In this configuration, when the rotary rack 72 is rotated by the rotation driving unit 78, the cavity resonator 11 is rotated, and thereby the body 10 can be heated in an arbitrary direction or can be heated while rotated.

Figures 19A, 19B:
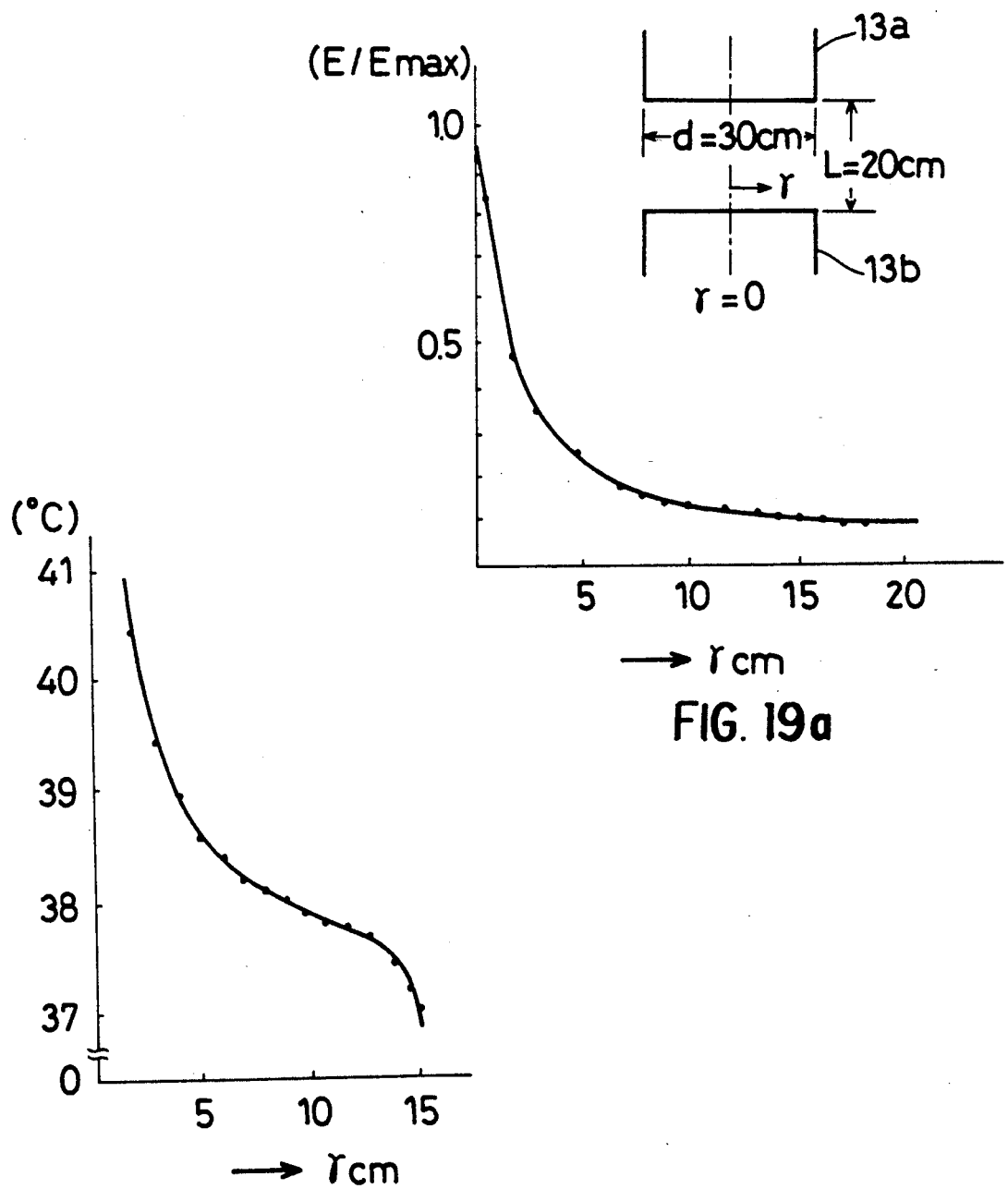
FIG. 19a is a graphic plot of electric field intensity as a function of the distance of the inner protrusions from the center axis of the cavity resonator.
FIG. 19b is a graphic plot of temperature as a function of the distance of the inner protrusions from the center axis; and, FIG. 20 illustrates a prior art local heating apparatus employing current for heating a body during treatment for cancer.

FIGS. 19a and 19b show the results of heating experiments conducted with the local heating apparatus of the present invention. The diameter of the inner protrusions 13a and 13b is 30 cm, the interval between the protrusions is 20 cm, and the frequency is 140.75 MHz. FIG. 19a shows a distribution of electric field intensity, and the ordinate represents the electric field intensity and the abscissa represents the distance of the inner protrusions 13a and 13b from the center axis. FIG. 19b shows a temperature distribution, and the ordinate represents the temperature and the abscissa represents the distance of the inner protrusion 13a and 13b from the center axis.

The results of the experiments show that the temperature becomes highest on the center axis of the inner protrusion 13a and 13b, and the electric field is converged and concentrated on the center axis. Also, in the heating experiments wherein fat and muscles are sandwiched in a superposed fashion, fat is hardly heated, and muscles are heated intensely, and thereby desirable results have been obtained for medical treatment.

From the foregoing description it is seen that a cavity resonator for local heating and a local heating apparatus constructed in accordance with the present invention are useful for heating a human body, and are specifically suitable for destroying cancer cells by heat treatment.

We claim:

1. A cavity resonator responsive to high-frequency energy for locally heating a body inserted therein, said cavity resonator comprising:
   electrically conductive walls means forming an enclosed cavity, said conductive wall means capable of conducting a current and thereby creating a magnetic field when said cavity resonator is supplied with high-frequency energy;
   at least one electrically conductive protrusion protruding from, and electrically continuous with, said wall means for protruding partly into said cavity to thereby define an empty space between said protrusion and said wall means opposite to said protrusion, said space being adapted to receive at least that part of a body to be inserted therein which is to be locally heated;
   said wall means and said at lest one protrusion forming an electrically resonant structure capable of generating, in response to appropriate high-frequency energy supplied to said cavity resonator, a standing wave electric field in all of said space along the axis of said at least one protrusion, said electric field being confined by said magnetic field.

2. A cavity resonator as claimed in claim 1 wherein said at least one protrusion is formed as part of the wall means of said cavity.

3. A cavity resonator as claimed in claim 1 wherein said space is formed between opposing protrusions from opposing sides of said wall means.

4. A cavity resonator as claimed in claim 1 wherein said cavity has a cylindrical shape with two opposing end surfaces and wherein each of said end surface has a protrusion.

5. A cavity resonator as claimed in claim 1 wherein said cavity is cylindrical in shape and said at least one protrusion comprises a hollow cylindrical conductor.

6. A cavity resonator as claimed in claim 1 wherein said cavity has opposing end surfaces, said cavity resonator further comprising means for slidingly supporting at least one of said protrusions in one of said end surfaces while maintaining electrical contact therewith.

7. A cavity resonator as claimed in claim 1 wherein said cavity has a lateral wall and opposing end surfaces supporting at least one of said protrusions, at least one of said end surfaces being movable relative to said lateral wall.

8. A cavity resonator as claimed in claim 1 wherein said at least one protrusion comprises a conductor having an end surface covered by an insulating member.

9. A cavity resonator as claimed in claim 1 wherein said at least one protrusion has an end surface containing surface discontinuities for varying the distribution of the standing wave electric field in said space.

10. A cavity resonator as claimed in claim 1 further including at least one electric field adjusting member inserted in said cavity outside of said space for adjusting the distribution of the standing waveelectric field in said space.

11. Apparatus as claimed in claim 1 further comprising frequency adjusting means movable into and out of said cavity to adjust the resonance frequency of the cavity resonator, a resonant state detecting means for detecting the resonance state of said cavity resonator, and means responsive to said detecting means for moving said frequency adjusting means.

12. Apparatus as claimed in claim 1 and further comprising cooling means surrounding said at least one protrusion, and a cooling unit for supplying cool water to said cooling means.

13. Apparatus according to claim 1 and further comprising a table for supporting said body in said cavity and means for rotating said cavity resonator about said table.

* * * * *